(12) United States Patent
Faurie et al.

(10) Patent No.: US 9,962,457 B2
(45) Date of Patent: May 8, 2018

(54) METHOD AND DEVICE FOR PURIFICATION AND DEODORIZATION OF AIR

(71) Applicant: LOUTI, Dommartin (FR)

(72) Inventors: Jean-Michel Faurie, Dommartin (FR); Didier Chavanon, St Just Chaleyssin (FR)

(73) Assignee: LOUTI, Dommartin (FR)

( * ) Notice: Subject to any disclaimer, the term of this patent is extended or adjusted under 35 U.S.C. 154(b) by 684 days.

(21) Appl. No.: 14/347,834

(22) PCT Filed: Sep. 26, 2012

(86) PCT No.: PCT/EP2012/069005
§ 371 (c)(1),
(2) Date: Mar. 27, 2014

(87) PCT Pub. No.: WO2013/045515
PCT Pub. Date: Apr. 4, 2013

(65) Prior Publication Data
US 2014/0234163 A1    Aug. 21, 2014

(30) Foreign Application Priority Data

Sep. 27, 2011   (FR) ...................................... 11 58657

(51) Int. Cl.
*A61L 9/20* (2006.01)
*F24F 3/16* (2006.01)

(52) U.S. Cl.
CPC ................. *A61L 9/20* (2013.01); *A61L 9/205* (2013.01); *A61L 2209/212* (2013.01); *F24F 2003/1667* (2013.01)

(58) Field of Classification Search
CPC ...... A61L 9/20; A61L 9/205; A61L 2209/212; F24F 2003/1667
See application file for complete search history.

(56) References Cited

U.S. PATENT DOCUMENTS

| | | | |
|---|---|---|---|
| 5,136,170 A * | 8/1992 | Gellert | H01J 65/046 250/492.1 |
| 6,589,489 B2 | 7/2003 | Morrow et al. | |
| 6,797,127 B1 | 9/2004 | Murata et al. | |
| 2003/0113246 A1 | 6/2003 | Saitou et al. | |
| 2010/0003164 A1* | 1/2010 | Bourne | A61L 9/205 422/4 |

FOREIGN PATENT DOCUMENTS

| | | |
|---|---|---|
| FR | 2892951 A1 | 5/2007 |
| JP | 2005342506 A | 12/2005 |

OTHER PUBLICATIONS

International Search report for PCT/EP2012/069005 dated Dec. 14, 2012.

* cited by examiner

*Primary Examiner* — Sean E Conley
(74) *Attorney, Agent, or Firm* — B. Aaron Schulman, Esq.; Stites & Harbison, PLLC (57) ABSTRACT

The present invention relates to a method for purification of air, comprising the degradation of all or some of the pollutants by the action of UV rays that are obtained by means of a single light source emitting rays at 254 nm and rays at 185 nm, and optionally UVA rays, and by photocatalysis, the ratio of the amount of energy 185 to the amount of energy 254 ranging from 0.01 to 1. The present invention also relates to a device allowing said method to be carried out.

13 Claims, 3 Drawing Sheets

METHOD AND DEVICE FOR PURIFICATION AND DEODORIZATION OF AIR

This application is a National Stage application of PCT international application PCT/EP2012/069005, filed on Sep. 26, 2012 which claims the priority of French Patent Application No. 11 58657 entitled "METHOD AND DEVICE FOR PURIFICATION AND DEODORIZATION OF AIR", filed with the European Patent Office on Sep. 27, 2011, both of which are incorporated herein by reference in their entirety.

The present invention relates to a method for purification and/or deodorization of air. The invention also relates to a device allowing application of this method.

Improvement of the quality of air becomes a major issue for public health authorities. It may notably pass through purification of air.

Many methods have been described for purifying air.

Notably from WO02/47799, a device for purifying air is known comprising a source of UV radiation and a photocatalyst. From WO2010/130965, a device for purifying air is also known comprising a filtering medium comprising a photocatalysis cell having a photocatalytic filter intended to be irradiated with a light source (254 nm) for scavenging chemical and/or microbiological pollutants. From WO2008/122871, the combination of a photocatalytic treatment and scavenging of particles for purifying air is known. The use of a light source emitting rays from 250 to 270 nm is described as having a germicidal effect. Finally from WO2004/081458, an air filtering device is known, comprising an adsorption agent (active coal) a photocatalyst agent ($TiO_2$) and means for illuminating the photocatalyst agent, these elements being contained in two distinct modules.

However, the already known methods and devices do not allow sufficiently effective purifying of air. A recent study (Enc. Risque Sante, 2011, Vol. 10, No. 1 35-45) has shown that the methods of the state of the art generate, by degradation of the pollutants initially present in air, other pollutants which are not degraded. Certain devices of the state of the art also emit ozone and/or NOx.

Methods for treating air and installations for applying these methods notably for purification of air are also known notably from U.S. Pat. No. 6,589,489 and JP 2005342509, notably comprising the degradation by ozone of the pollutants contained in the air. The ozone being produced by means of a lamp notably emitting radiations at 185 nm. The lamps applied in these methods are lamps emitting radiation from 185 to 350 nm. The lamps are used in all the stages of the air treatment system, the ozone being therefore produced in all the stages of the installation. The generated amount of ozone is therefore significant and the risk of releasing ozone outside the device is also significant or even systematic. In order to limit the amount of ozone produced and the risks of release of the ozone outside the device, it is then necessary to apply in the known devices, complex systems; for example catalytic systems allow adsorption of ozone or filters allowing radiations at 185 nm to be retained on certain portions of the device thereby limiting the production of ozone.

A reduction in the power of the lamp will have as a consequence the reduction of the power of the other radiations, notably radiations at 254 nm which by photocatalysis allow decomposition of the pollutants comprised in the air to be treated. Less efficient decontamination would result from this.

Therefore there is a benefit of providing an improved method for purifying air as compared with the known methods of the state of the art.

An object of the present invention is to provide a method for purifying air which is efficient, applicable to industry and economical, not requiring any complex application for removing ozone.

An object of the present invention is further to provide a method for purifying air producing a controlled amount of ozone allowing decomposition of the pollutants of the air.

Another object of the present invention is to provide a method for purification and/or deodorization of air which does not generate additional pollutants relatively to the pollutants initially contained in the air.

Another object of the present invention is to provide a method which may be used in home or general public applications, in industrial applications, in clean rooms, in hospital environments, in offices, etc.

Another object of the invention is to provide a device with a minimum size and allowing application of this method.

Other objects will further appear upon reading the description of the invention which follows.

These objects are achieved by the present invention which relates to a method for purification and/or deodorization of air comprising pollutants, comprising the degradation of all or part of the pollutants by the action of UV rays at 254 nm and of rays at 185 nm and by photocatalysis, the UV rays at 254 nm and at 185 nm being emitted by a single light source, the ratio of the energy amount of rays at 185 nm over the amount of energy of rays at 254 nm ranging from 0.01 to 1.

Preferably, the ratio, for the single source, of the amount of energy of the rays at 185 nm over the amount of the energy of the rays at 254 nm ranges from 0.01 to 0.3, preferably ranges from 0.01 to 0.2, more preferably ranges from 0.005 to 0.05.

Preferably, the ratio for the single light source, of the amount of energy of the rays at 185 nm over the amount of the energy of the rays at 254 nm ranges from 0.01 to 1, preferably from 0.01 to 0.3, preferably ranges from 0.01 to 0.2, more preferably ranges from 0.005 to 0.05 for a pollutant concentration ranging from 1 to 5,000 ppm, preferably from 1 to 100 ppm, more preferably from 1 ppb to 10 ppm.

As explained further on, these ratios are obtained by applying a single light source consisting of two quartz, one emitting rays at 185 nm and at 254 nm and the other one only emitting rays at 254 nm.

The method according to the invention may further comprise degradation of the pollutants contained in the air by the action of UVA rays.

The UVA rays may stem from a distinct light source or from the single source then emitting rays at 185 nm, at 254 nm and UVA rays, the single source then has a ratio of the energy amount of the rays at 185 nm over the amount of energy of the rays at 254 nm and of the UVA rays ranging from 0.01 to 1, preferably ranging from 0.01 to 0.3, preferably ranging from 0.01 to 0.2, preferably ranging from 0.005 to 0.05. Preferably, the single source then has a ratio of the energy amount of the rays at 185 nm over the energy amount of the rays at 254 nm and of the UVA rays ranging from 0.01. to 1, preferably ranging from 0.01 to 0.3, preferably ranging from 0.01 to 0.2, preferably ranging from 0.005 to 0.05 for a pollutant concentration ranging from 1 to 5,000 ppm, preferably from 1 to 100 ppm, preferably from 1 to 100 ppm, more preferably from 1 ppb to 10 ppm.

The light sources are notably diodes, light emitting diodes (LED) or lamps.

By a ray at 254 nm, is meant all the rays having a wavelength close to 254 nm, notably rays having a wavelength comprised between 250 and 260 nm. More particularly, by rays at 254 nm, the present invention also means coverage of the rays at 253.7 nm usually obtained by the use of standard light sources at 254 nm.

The UVA rays are notably rays at 365 nm. By rays at 365 nm, are meant all the rays having a wavelength close to 365 nm, notably rays having a wavelength comprised between 350 and 375 nm.

Within the scope of the present invention, by air purification is meant the treatment of air for degrading the pollutants which may be contained in this air. By air purification is also meant sterilization of the air aiming at degradation of bacteria and viruses which may be contained in this air.

Within the scope of this invention, by deodorization of air is meant the treatment of air for suppressing odors, for example food odors, industrial waste odors, solvent odors, etc.

Within the scope of the present invention, by pollutants are meant all chemical, physical and/or biological products which may be contained in the air and which should be suppressed. These pollutants may be harmful products for the environment, for human or animal health; they may also be harmful or noxious products within the scope of particular activities, for example in hospital wards which should have very low or even zero thresholds of pollutants, notably bacteria, in clean rooms, but also in cold rooms, (notably for preserving foodstuffs), rooms for raising animals, rooms of a dwelling.

Preferably, the chemical pollutants are notably allergens, formaldehyde or a pollutant selected from the group of volatile organic compounds (VOC) such as for example ethylene, acetone, toluene, acetaldehyde, xylene and ethane.

Preferably, the biological pollutants are bacteria, fungi and viruses.

Advantageously, the rays of wavelength of 254 nm notably allow degradation of biological pollutants, notably of the virus and bacteria type.

The method therefore comprises a step for total or partial degradation of the pollutants of the air by ozonolysis. In this particular case, the ozone stems from the reaction of the oxygen contained in the air with rays having a wavelength of 185 nm.

Advantageously, ozonolysis allows greater degradation of the pollutants of the air.

In a particularly advantageous way, in the method of the invention, controlling the amount of energy corresponding to the 185 nm wavelength radiation allows control of the amount of ozone formed in order not to release or only release very little ozone at the end of the purification method of the invention.

Advantageously, the amount of energy corresponding to the 185 nm radiation is controlled so that the method does not release any ozone, the ozone produced by reaction of oxygen with the 185 nm radiations being totally consumed for degrading the pollutants and for the photocatalysis reaction.

To do this, the single light source emitting rays at 185 nm and at 254 nm consists of two quartzes, a first quartz emitting rays at 254 nm and 185 nm and if necessary UVA rays (in the case of a single source emitting rays at 185 nm, at 254 nm and UVA rays) and a second quartz emitting rays at 254 nm or if necessary rays at 254 nm and UVA rays. The quartz emitting rays at 254 nm and 185 nm and if necessary UVA rays has a length and a surface less than the one only emitting rays at 254 nm or if necessary only rays at 254 nm and UVA rays. For example, in the case of a single source, the single source may be a biquartz lamp of 254 nm and 185 nm for which the length of the surface of the quartz emitting rays at 185 nm and 254 nm is reduced relatively to the length of the quartz only emitting rays at 254 nm. This length of quartz emitting rays at 185 nm and at 254 nm and optionally UVAs is adjusted or adapted notably relatively to the passing air flow and to the types of pollutants to be removed.

Generally, the single light source as well as all the other sources described in the present invention may also emit rays in the visible spectrum.

Preferably, the amount of energy corresponding to the radiation with a wavelength of 185 nm ranges from 0.05 to 100 W, preferably from 0.1 to 100 W, preferably from 0.1 to 15 W, preferably from 0.5 to 15 W for a pollutant concentration ranging from 1 to 5,000 ppm, preferably from 1 pbb to 100 ppm.

Preferably, the amount of energy corresponding to the 185 nm radiation ranges from 1 to 100 W, preferably from 1 to 25 W, preferably from 0.05 to 25 W, for an inflowing air flow rate ranging from 1 to 5,000 m$^3$/h, preferably from 1 to 1,000 m$^3$/h.

The method of the present invention may further comprise one or several of the following steps, depending on the degree of purity of the air which is envisaged:
  degradation of the pollutants by the action of UV rays, notably UVC rays; and/or
  degradation of the pollutants by the action of UV rays, notably UVA rays; and/or
  degradation of the pollutants with another photocatalysis step; and/or
  scavenging of the pollutants by adsorption on an adsorption supporting medium;
each of these steps may be applied several times independently of each other and may be combined.

Thus, and preferably, the method according to the invention may further comprise, depending on the degree of purity of the air which is envisaged:
  degradation of the pollutants by the action of UV rays, notably of UVC rays; or
  degradation of the pollutants by the action of UV rays, notably UVA rays; or
  degradation of the pollutants with another photocatalysis step; or
  scavenging of the pollutants by adsorption on an adsorption supporting medium; or
  degradation of the pollutants by the action of UVC rays and by the action of UVA rays; or
  degradation of the pollutants by the action of UVC rays, by the action of UVA rays, and degradation of the pollutants with another photocatalysis step; or
  degradation of the pollutants by the action of UVC rays, by the action of UVA rays, and scavenging of the pollutants by adsorption on an adsorption supporting medium; or
  degradation of the pollutants by the action of UVC rays, by the action of UVA rays, the degradation of the pollutants with another photocatalysis step and scavenging of the pollutants by adsorption on an adsorption supporting medium; or
  degradation of the pollutants by the action of UVC rays and degradation of the pollutants with another photocatalysis step; or
  degradation of the pollutants by the action of UVC rays, degradation of the pollutants with another photocatalysis step and scavenging of the pollutants by adsorption on an adsorption supporting medium; or degradation of the pollutants by the action of UVC rays and scavenging of the pollutants by adsorption on an adsorption supporting medium; or degradation of the pollutants by the action of UVA rays, and degradation of the pollutants with another photocatalysis step; or degradation of the pollutants by the action of UVA rays, degradation of the pollutants with another photocatalysis step and scavenging of the pollutants by adsorption on an adsorption supporting medium; or degradation of the pollutants by the action of UVA rays, and scavenging of the pollutants by adsorption on an adsorption supporting medium; or degradation of the pollutants with another photocatalysis step and scavenging of the pollutants by adsorption on an adsorption supporting medium.

In a known way, the UVC rays are notably rays at 254 nm and the UVA rays are notably rays at 365 nm.

It should be understood that in the methods of the present invention, the UVC and UVA rays acting in the additional steps may stem from at least one other light source or from all or part of the quartz of the single source emitting rays at 254 nm and if necessary UVA rays. The single source emitting rays at 185 nm, 254 nm and UVA rays is then as characterized above.

Thus, the present invention intends to cover the combinations of steps conducted with the sole single source by the action of the different rays which it emits as well as combinations of steps conducted with the single source and other light sources.

Photocatalysis is generally applied by the action of UV rays in the presence of a catalyst. The photocatalysis therefore requires the presence of at least one light source. Preferably, the UV rays are UVC and/or UVA rays, preferably rays at 254 nm and/or 365 nm, for example rays with a wavelength of 254 nm.

The catalyst is selected from supported or unsupported photocatalysts notably from among semi-conductors. For example, the catalyst comprises titanium or tungsten. Preferably, the catalyst is supported or unsupported titanium dioxide. The support may notably be paper; silica or compounds comprising silica, for example quartz; fabrics, notably glass fabrics, for example quartz and silica fabrics; glass fibers; glass fiber fabrics; optical fiber fabrics; ceramics; or an assembly of these supports. Preferably, the support is an assembly of glass and paper fabrics.

Deposition of the catalyst on the support may be accomplished in any way known to one skilled in the art. It may notably be carried out by spraying the catalyst on the support or by soaking the support in a solution of catalysts or further by means of a high power pulsed magnetron, or further by deposition of layers of atoms. Preferably, the deposition of the catalyst is carried out by spraying the catalyst on the support or by soaking the support in a solution of catalysts or further by means of a high power pulsed magnetron.

The application or not of the steps for scavenging the pollutants may be determined by one skilled in the art notably depending on the pollutants contained in the air, on their degradation degree, notably if they produce undesirable or noxious byproducts during their degradation, on the desired purification level, on the type of contemplated application. For example, for an industrial application, scavenging of the residual pollutants with an adsorption supporting medium will not necessarily be useful while it will be useful in applications requiring a more intensive treatment of the air, for example in medical applications. Advantageously, the adsorption supporting medium allows scavenging of the residual ozone which would not have been consumed during the degradation of the pollutants and thus releasing air without or almost without any ozone. The adsorption supporting medium may also scavenge the pollutants which would not have been degraded or not completely degraded. Thus and advantageously, the scavenging step allows fine treatment of the air and thus improvement in the quality of the air at the output and therefore the obtaining of highly depolluted air.

The adsorption supporting medium may be selected from all porous materials which may adsorb pollutants and optionally ozone and having strong adsorbing power. The adsorption supporting medium may notably be selected from active coals; zeolites; xerogels, notably xerogels based on silica; or mixtures thereof.

Advantageously, the adsorption supporting medium is regenerated by the residual ozone, optionally present, which will degrade the pollutants which are adsorbed at its surface.

In a first particular embodiment, the method (P1) according to the invention comprises the following steps:

1) degradation of the pollutants by ozonolysis, by the action of the UV rays obtained by means of a single light source emitting rays with a wavelength of 254 nm and rays at 185 nm and by photocatalysis, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05;

2) scavenging of the residual pollutants on an adsorption supporting medium.

In a second particular embodiment, the method (P2) according to the invention comprises the following steps:

1) degradation of the pollutants by ozonolysis, by the action of UV rays obtained by means of a single light source emitting rays at 254 nm and rays at 185 nm, and by photocatalysis, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05;

2) degradation of the residual pollutants with another photocatalysis step.

In a third particular embodiment, the method (P3) according to the invention comprises the following steps:

1) degradation of the pollutants by ozonolysis, by the action of UV rays obtained by means of a single light source emitting rays at 254 nm and rays at 185 nm and by photocatalysis, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05;

2) degradation of the residual pollutants with another photocatalysis step;

3) scavenging of the residual pollutants on an adsorption supporting medium.

In a fourth particular embodiment, the method (P4) according to the invention comprises the following steps:

1) degradation of the pollutants by ozonolysis, by the action of the UV rays obtained by means of a single light source emitting rays at 254 nm and rays at 185 nm and by photocatalysis, the ratio of the energy amount of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05;

2) degradation of the residual pollutants by the action of the UVC rays;

3) optionally scavenging of the residual pollutants on an adsorption supporting medium.

In a fifth particular embodiment, the method (P5) according to the invention comprises the following steps:

1) degradation of the pollutants by ozonolysis, by the action of UV rays obtained by means of a single light source emitting rays at 254 nm and rays of 185 nm and by photocatalysis, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05;

2) degradation of the residual pollutants by the action of UVA rays;

3) optionally scavenging of the residual pollutants on an adsorption supporting medium.

In a sixth particular embodiment, the method (P6) according to the invention comprises the following steps:

1) degradation of the pollutants by ozonolysis, by the action of UV rays obtained by means of a single light source emitting rays at 254 nm and rays at 185 nm and by photocatalysis, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05;

2) degradation of the residual pollutants by the action of UVC rays;

3) degradation of the residual pollutants by the action of UVA rays;

4) optionally scavenging of the residual pollutants on an adsorption supporting medium.

In a seventh embodiment (P7), an additional photocatalysis step may be applied between the steps (2) and (3) of the methods (P4), (P5) and (P6).

In an eighth particular embodiment, the method (P8) according to the invention comprises the following steps:

1) degradation of the pollutants by ozonolysis, by the action of UV rays obtained by means of a single light source emitting rays at 254 nm and rays at 185 nm and by photocatalysis, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05;

2) degradation of the residual pollutants with another photocatalysis step;

3) degradation of the residual pollutants by the action of UVC rays;

4) optionally the scavenging of the residual pollutants on an adsorption supporting medium, steps (2) and (3) may be conducted simultaneously. Preferably, steps (2) and (3) are conducted simultaneously.

In a ninth particular embodiment, the method (P9) according to the invention comprises the following steps:

1) degradation of the pollutants by ozonolysis, by the action of UV rays obtained by means of a single light source emitting rays at 254 nm and rays at 185 nm and by photocatalysis, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05;

2) degradation of the residual pollutants with another photocatalysis step;

3) degradation of the residual pollutants by the action of UVA rays;

4) optionally scavenging of the residual pollutants on an adsorption supporting medium, steps (2) and (3) may be conducted simultaneously.

Preferably, the steps (2) and (3) are conducted simultaneously.

In a tenth particular embodiment, the method (P10) according to the invention comprises the following steps:

1) degradation of the pollutants by ozonolysis, by the action of UV rays obtained by means of a single light source emitting rays at 254 nm and rays at 185 nm and by photocatalysis, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05;

2) degradation of the residual pollutants with another photocatalysis step;

3) degradation of the residual pollutants by the action of UVC rays;

4) degradation of the residual pollutants by the action of UVA rays;

5) optionally scavenging of the residual pollutants on an adsorption supporting medium, the steps (2), (3) and (4) may be conducted simultaneously.

Preferably, the steps (2), (3), and (4) are conducted simultaneously.

In an eleventh embodiment (P11), an additional photocatalysis step may be applied between steps (3) and (4) of the methods (P8) and (P9) and between the steps (4) and (5) of the method (P10).

It should be understood that in the methods (P1) to (P11), the UVC and UVA rays acting in the additional steps (2), (3) and/or (4) may stem from at least one other light source or from all or part of the quartz of the single source emitting rays at 254 nm and if necessary UVA rays. The single source emitting rays at 185 nm, 254 nm and UVA rays is as defined above.

Thus, the present invention intends to cover the combinations of steps conducted with the single source alone by the action of different rays which its emits as well as combinations of steps conducted with the single source and other light sources.

Advantageously, the method according to the invention as well as the method according to each of the particular embodiments may further comprise a preliminary step for mechanical filtering of the air allowing retention of the largest impurities in terms of size. This mechanical filtration may be achieved by any mechanical filter known to one skilled in the art, notably by means of a mechanical filter of the G type (G1 to G4) defined according to the EN 779-2002 standard, preferably by means of a G3 filter; of the HEPA type or of the ULPA type defined according to the EN 1822 standard.

The method of the present invention advantageously allows very fine purification of the air, the totality or the quasi-totality of the pollutants being degraded or scavenged. Advantageously, and unlike the method of the state of the art, the method of the invention also allows degradation of byproducts from the degradation of the pollutants. This is notably due to the combination of the different steps of the method according to the invention.

Advantageously, the method of the invention allows recovery, after treatment, of depolluted air for example meeting the specificities of the AFNOR XP B44-13 standard and comprising no or very little ozone, preferably between 0.005 and 0.05 ppm of ozone, for example between 0.01 and 0.05 ppm of ozone.

The method of the invention may notably be applied in a home application for the treatment of air, in a medical application of the treatment of air, in very extensive applications of the treatment of air. The method of the present invention may thus and advantageously be applied for treating air in hospital wards, clean rooms, cold rooms, rooms for raising animals, rooms in the home, rooms of a dwelling, offices, etc., and for treating industrial effluents.

The method of the invention may also be advantageously used for deodorization of the air, notably in the aforementioned applications, for example for treating food odors, industrial effluents, odors of solvents, etc.

The invention also relates to a device for applying the method according to the invention comprising a chamber (1) comprising a single light source emitting rays at 254 nm and rays at 185 nm, and a photocatalyst, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05.

Preferably, the ratio for the single source, of the amount of energy of the rays at 185 nm over the amount of energy of the rays at 254 nm ranges from 0.01 to 0.3, preferably ranges from 0.01 to 0.2, notably ranges from 0.005 to 0.05.

Preferably, the ratio for the single source, of the amount of energy of the rays at 185 nm over the amount of energy of the rays at 254 nm, ranges from 0.01 to 1, preferably ranges from 0.01 to 0.3, preferably ranges from 0.01 to 0.2, notably ranges from 0.005 to 0.05, for a pollutant concentration ranging from 1 to 5,000 ppm, preferably from 1 ppb to 100 ppm.

The device of the present invention may further comprise in the chamber (1) an adsorption supporting medium.

The single source according to the invention may also emit UVA rays, then emitting rays at 185 nm, 254 nm and UVA rays, the ratio of the amount of energy of the rays at 185 nm over the energy amount of the rays at 254 nm and of the UVA rays ranging from 0.01 to 1, preferably ranging from 0.01 to 0.3, preferably ranging from 0.01 to 0.2, notably ranging from 0.005 to 0.05; preferably ranging from 0.01 to 1, preferably ranging from 0.01 to 0.3, preferably ranging from 0.01 to 0.2, notably ranging from 0.005 to 0.05 for a pollutant concentration ranging from 1 to 5,000 ppm, preferably ranging from 1 ppb to 100 ppm.

The device of the present invention may further comprise in the chamber (1) another light source emitting UVA rays.

The device of the present invention may further comprise a chamber (2) comprising:
- at least one other light source emitting UVC rays; or
- at least one other light source emitting UVA rays; or
- at least one other light source emitting UVC rays and at least one other source emitting UVA rays; or
- at least one other light source emitting UVC rays and a photocatalyst; or
- at least one other light source emitting UVA rays and a photocatalyst; or
- at least one other light source emitting UVC rays, at least one other light source emitting UVA rays and a photocatalyst; or
- at least one other light source emitting UVC rays and an adsorption supporting medium; or
- at least one other light source emitting UVA rays and an adsorption supporting medium; or
- at least one other light source emitting UVC rays, at least one other light source emitting UVA rays and an adsorption supporting medium; or
- at least one other light source emitting UVC rays, a photocatalyst and an adsorption supporting medium; or
- at least one other light source emitting UVA rays, a photocatalyst and an adsorption supporting medium; or
- at least one other light source emitting UVA rays, at least one other light source emitting UVC rays, a photocatalyst and an adsorption supporting medium;
- an adsorption supporting medium,
- all or part of the quartz of the single source only emitting rays at 254 nm and if necessary only rays at 254 nm and UVA rays and a photocatalyst,
- all or part of the quartz of the single source only emitting rays at 254 nm and if necessary only rays at 254 nm and UVA rays, a photocatalyst and an adsorption supporting medium,
- all or part of the quartz of the single source only emitting rays at 254 nm and if necessary only rays at 254 nm and UVA rays, another light source emitting rays at 254 nm or UVA rays, notably UVA rays, and a photocatalyst,
- all or part of the quartz of the single source only emitting rays at 254 nm and if necessary only rays at 254 nm and UVA rays, another light source emitting rays at 254 nm or UVA rays, notably UVA rays, a photocatalyst and an adsorption supporting medium.

Preferably, the device of the invention may comprise a chamber (2) comprising:
- a photocatalyst; or
- an adsorption supporting medium; or
- a photocatalyst and an adsorption supporting medium, all or part of the quartz of the single source only emitting rays at 254 nm and if necessary only rays at 254 nm and UVA rays.

The device according to the invention may further comprise one or several other chambers comprising:
- at least one other light source emitting UVC rays; or
- at least one other light source emitting UVA rays; or
- at least one other light source emitting UVC rays and at least one other source emitting UVA rays; or
- at least one other light source emitting UVC rays and a photocatalyst; or
- at least one other light source emitting UVA rays and a photocatalyst; or
- at least one other light source emitting UVC rays, at least one other light source emitting UVA rays and a photocatalyst; or
- at least one other light source emitting UVC rays and an adsorption supporting medium; or
- at least one other light source emitting UVA rays and an adsorption supporting medium; or
- at least one other light source emitting UVC rays, at least one other light source emitting UVA rays and an adsorption supporting medium; or
- at least one other light source emitting UVC rays, a photocatalyst and an adsorption supporting medium; or
- at least one other light source emitting UVA rays, a photocatalyst and an adsorption supporting medium; or
- at least one other light source emitting UVA rays, at least one other light source emitting UVC rays, a photocatalyst and an adsorption supporting medium;
- an adsorption supporting medium, all or part of the quartz of the single source only emitting rays at 254 nm and if necessary only rays at 254 nm and UVA rays and a photocatalyst, all or part of the quartz of the single source only emitting rays at 254 nm and if necessary only rays at 254 nm and UVA rays, a photocatalyst and an adsorption supporting medium, all or part of the quartz of the single source only emitting rays at 254 nm and if necessary only rays at 254 nm and UVA rays, another light source emitting rays at 254 nm or UVA rays, notably rays at 365 nm, and a photocatalyst, all or part of the quartz of the single source only emitting rays at 254 nm and if necessary only rays at 254 nm and UVA rays, another light source emitting rays at 254 nm or UVA rays, notably UVA rays, a photocatalyst and an adsorption supporting medium.

The single source is as defined above.

Preferably, the device of the invention may further comprise one or several other chambers comprising:
a photocatalyst; or
an adsorption supporting medium; or
a photocatalyst and an adsorption supporting medium,
all or part of the quartz of the single source only emitting rays at 254 nm and if necessary only rays at 254 nm and UVA rays.

Preferably in the device of the invention, the ratio of the amount of energy of the rays at 185 nm over the amount of energy of the rays at 254 nm ranges from 0.01 to 0.3, preferably ranges from 0.01 to 0.2, notably ranges from 0.005 to 0.05.

Preferably, the ratio of the amount of energy of the rays at 185 nm over the amount of energy of the rays at 254 nm ranges from 0.01 to 1, preferably ranges from 0.01 to 0.3, preferably ranges from 0.01 to 0.2, notably ranges from 0.051 to 0.05 for a pollutant concentration ranging from 1 to 5,000 ppm, preferably ranging from 1 ppb to 100 ppm.

Preferably, the ratio of the amount of energy of the rays at 185 nm over the amount of energy of the rays at 254 nm and of the UVA rays ranging from 0.01 to 1, preferably ranging from 0.01 to 0.3, preferably ranging from 0.01 to 0.2, preferably ranging from 0.005 to 0.05. Preferably, the single source then has a ratio of the amount of energy of the rays to 185 nm over the amount of energy of the rays at 254 nm and of the UVA rays ranging from 0.01 to 1, preferably ranging from 0.01 to 0.3, preferably ranging from 0.01 to 0.2, preferably ranging from 0.005 to 0.05 for a pollutant concentration ranging from 1 to 5,000 ppm, preferably from 1 to 100 ppm, more preferably from 1 ppb to 10 ppm.

In a first embodiment (A), the device according to the invention comprises a chamber (1) comprising a single light source emitting rays at 254 nm and rays at 185 nm, a photocatalyst, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05.

In a second embodiment (B), the device according to the invention comprises a chamber (1) comprising a single light source emitting rays at 254 nm and rays at 185 nm, a photocatalyst, and an adsorption supporting medium, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05.

In a third embodiment (C), the device according to the invention comprises:

a chamber (1) comprising a single light source emitting rays at 254 nm and rays at 185 nm, and a photocatalyst, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05.

a chamber (2) comprising at least one other light source emitting UVA and UVC rays, and optionally an adsorption supporting medium or comprising all or part of the quartz of the single source only emitting rays at 254 nm and if necessary only rays at 254 nm and UVA rays, and optionally an adsorption supporting medium.

In a fourth embodiment (D), the device according to the invention comprises:

a chamber (1) comprising a single light source emitting rays at 254 nm and rays at 185 nm, and a photocatalyst, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05;

a chamber (2) comprising at least one other light source emitting UVA and/or UVC rays, a photocatalyst, and optionally an adsorption supporting medium or comprising all or part of the quartz of the single source only emitting rays at 254 nm and if necessary only rays at 254 nm and UVA rays.

Preferably, it should be understood in the devices of the invention comprising several chambers and for which the chambers following, the chamber 1, comprise all or part of the quartz of the single source only emitting rays at 254 nm or if necessary only rays at 254 nm and UVA rays, that the single source begins in the first chamber in which is found the quartz emitting rays at 185 nm and rays at 254 nm or if necessary rays at 185 nm, rays at 254 nm and UVA rays, and extends into the other chambers. The first chamber may also comprise a portion of the quartz only emitting rays at 254 nm or if necessary only rays at 254 nm and UVA rays.

These particular devices preferably and advantageously allow limitation of the formation of ozone in the first chamber and therefore limitation or even suppression of the release of ozone outside the device.

The devices of the present invention do not exclude the presence of other light sources, notably emitting rays at 254 nm and UVA rays, in the different chambers.

In the devices of the invention, the single source may also emit UVA rays, the single source then emitting rays at 185 nm, 254 nm and UVA rays, the ratio of the amount of energy of the rays at 185 nm over the amount of energy of the rays at 254 nm and of the UVA rays ranging from 0.01 to 1, preferably ranging from 0.01 to 0.3, preferably ranging from 0.01 to 0.2, notably ranging from 0.005 to 0.05; preferably ranging from 0.01 to 1, preferably ranging from 0.01 to 0.3, preferably ranging from 0.01 to 0.2, notably ranging from 0.005 to 0.05 for a pollutant concentration ranging from 1 to 5,000 ppm, preferably ranging from 1 ppb to 100 ppm.

As regards the devices comprising a single chamber, the walls of this chamber are generally permeable to air. The photocatalyst totally or partly covers the internal wall of the chamber and the adsorption supporting medium, if it is present, covers the external wall of the chamber.

As regards the devices comprising at least two chambers, the latter may be concentric or juxtaposed to each other, the single source emitting UV rays at 254 nm, at 185 nm and if necessary UVA rays, is comprised in the first chamber in contact with the air to be treated. All or part of the quartz of the single source only emitting rays at 254 nm and if necessary only rays at 254 nm and UVA rays may extend into the other chambers.

This gives the possibility in the other chambers of the device of consuming the residual ozone for degradation of the pollutants or by adsorption. This advantageously gives the possibility of limiting or even avoiding release of ozone at the end of the process. In the case of concentric chambers, the single source emitting UV rays at 254 nm and at 185 nm is comprised in the internal chamber.

In the case when the chambers are concentric, they may for example be cylindrical. The walls of these chambers are permeable to air. The photocatalyst, if it is present, totally or partly covers the internal wall and the external wall of the chamber except for the external wall of the external chamber if an adsorption supporting medium is present, this adsorption supporting medium then totally or partly covering the external wall of the external chamber.

For example, in the case of a device comprising two concentric chambers (chamber (1) inside the chamber (2)) the photocatalyst covers the internal wall and the external wall of the chamber (1) as well as, if necessary, the internal wall of the chamber (2) and, if necessary, the adsorption supporting medium if it is present, covers the external wall of the chamber (2).

In the case when the chambers are juxtaposed, only the walls separating the different chambers from each other are permeable to air. The photocatalyst, if it is present, may totally or partly cover the internal walls of the chambers and/or totally or partly cover plates which are positioned inside the chamber so as to provide a passage for the air.

Advantageously, the plates extend transversely to a wall of the chamber in the direction of the opposite wall without attaining it, so as to provide a space between a plate and the opposite wall thereby allowing passage of the air. These plates are advantageously positioned in alternation (one plate in the direction of the lower wall and the next plate in the direction of the upper wall). This particular arrangement of the plates gives the possibility of forcing the air to pass in contact with the plates or nearby. This allows better destruction of the pollutants by photocatalysis.

Preferably, the chambers are concentric, the chamber (1) being found at the center of the other chamber(s).

In a preferred embodiment, the device according to the invention comprises two concentric chambers:
  an internal chamber (1) comprising a single light source emitting rays at 254 nm and 185 nm and a photocatalyst, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05; and
  an external chamber (2) comprising at least one second light source emitting rays at 254 nm, a photocatalyst and optionally an adsorption supporting medium, the walls of the chambers (1) and (2) being permeable to air.

Preferably, the photocatalyst covers the internal and external walls of the chamber (1) and the internal wall of the chamber (2) and the adsorption supporting medium covers the external wall of the chamber (2).

Preferably, the photocatalyst covers all or part of the internal and external walls of the chambers (1) as well as the internal wall of the chambers (2) and the adsorption supporting medium covers all or part of the external wall of the chamber (2).

In a preferred embodiment, the device according to the invention comprises two juxtaposed chambers:
  a chamber (1) comprising a single light source emitting rays at 254 nm and 185 nm, and a photocatalyst, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05; and
  a chamber (2) comprising at least one second light source rays at 254 nm a photocatalyst and optionally an adsorption supporting medium, only the walls separating the different chambers from each other are permeable to air.

In a preferred embodiment, the device of the invention comprises two juxtaposed chambers:
  a chamber (1) comprising a single light source emitting rays at 254 nm and 185 nm, and a photocatalyst, the ratio of the amount of energy of the rays at 185 nm over the amount of energy of the rays at 254 nm ranging from 0.01 to 1, preferably ranging from 0.01 to 0.3, preferably ranging from 0.01 to 0.2, notably ranging from 0.005 to 0.05; and
  a chamber (2) comprising all or part of the quartz of the single source only emitting rays at 254 nm, a photocatalyst and optionally an adsorption supporting medium.

only the walls separating the different chambers from each other are permeable to air.

The chamber (2) may optionally comprise other sources emitting rays at 254 nm.

Advantageously, the device according to the invention further comprises a mechanical filter for air.

FIG. 1 is a right handed view of FIG. 2.

Figure 1:
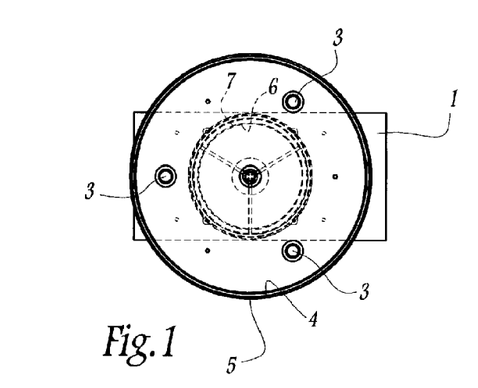
FIG. 1 illustrates a front view of a device comprising two concentric cylindrical chambers according to the invention.
Figure 2:
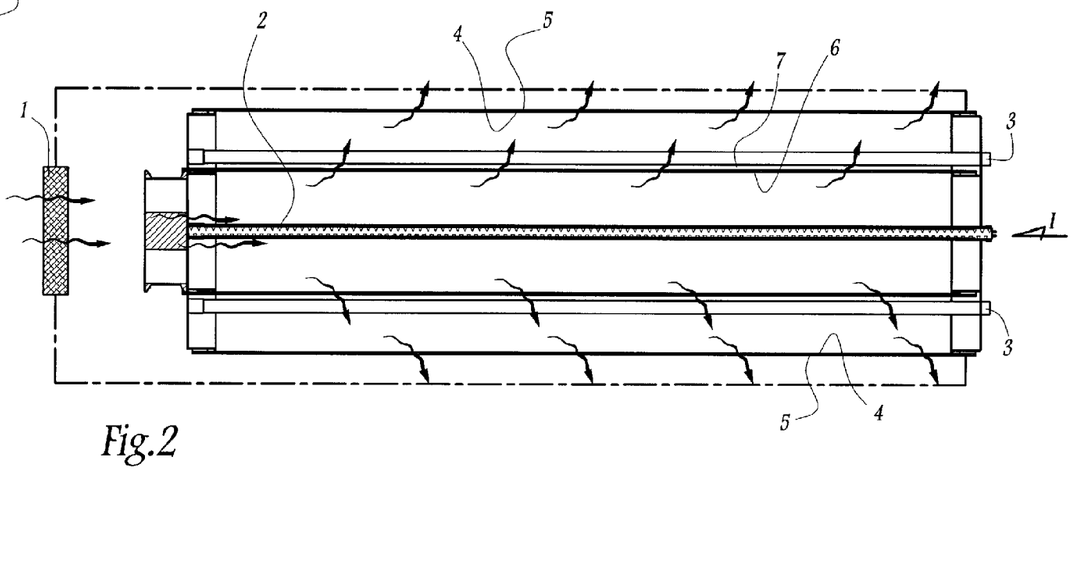
FIG. 2 illustrates a longitudinal section of a device comprising two concentric cylindrical chambers according to the invention.
Figure 3:
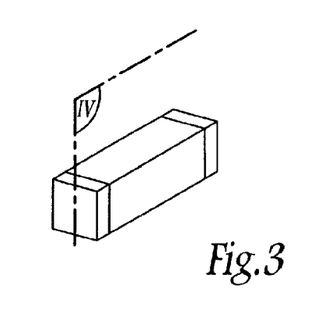
FIG. 3 illustrates a device comprising an assembly of juxtaposed chambers according to the invention.

FIG. 2 illustrates the device according to the invention comprising a mechanical filter (1) and two concentric cylindrical chambers comprising:
  a single biquartz lamp source (2) emitting radiations at 254 nm and rays at 185 nm located in the internal chamber;
  three lamps (3) (the third lamp being in the plane of the section) emitting radiation at 254 nm and/or at 365 nm located in the external chamber;
  a photocatalyst coating on the internal wall (4) of the external chamber and an adsorption supporting medium on the external wall (5) of the external chamber;
  a photocatalyst coating on the internal wall (6) and the external wall (7) of the internal chamber.

The air flows are materialized by the different arrows.

Figure 4:
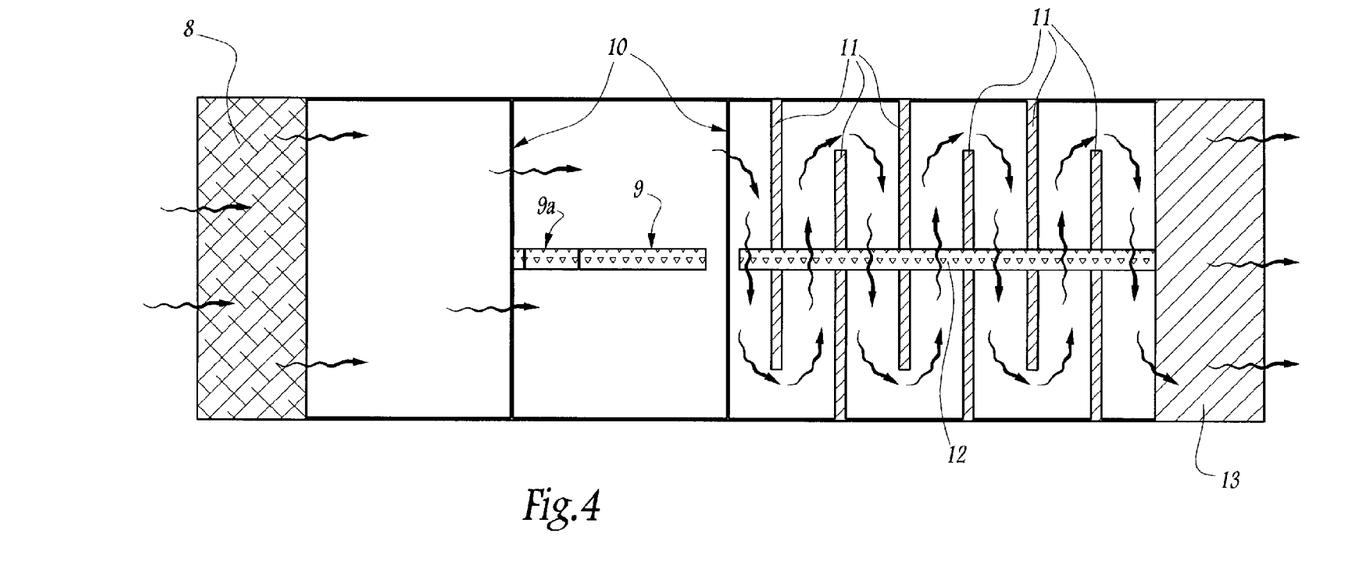
FIG. 4 illustrates a view along the sectional plane IV of the device according to claim 3.

FIG. 4 illustrates a device according to the invention comprising a mechanical filter (8) an adsorption supporting medium (13) and two juxtaposed chambers:
  a first chamber comprising a biquartz lamp (9) emitting rays at 254 nm and rays at 185 nm emitted by the portion (9a), the internal wall (10) of this chamber being covered with a photocatalyst; and a second chamber comprising a lamp emitting rays at 254 nm and/or 365 nm (12) and plates (11), the surface of which is covered with a photocatalyst.

The air flows are materialized by the different arrows. The air flow comes into contact with or near the plates (11).

Figure 5:
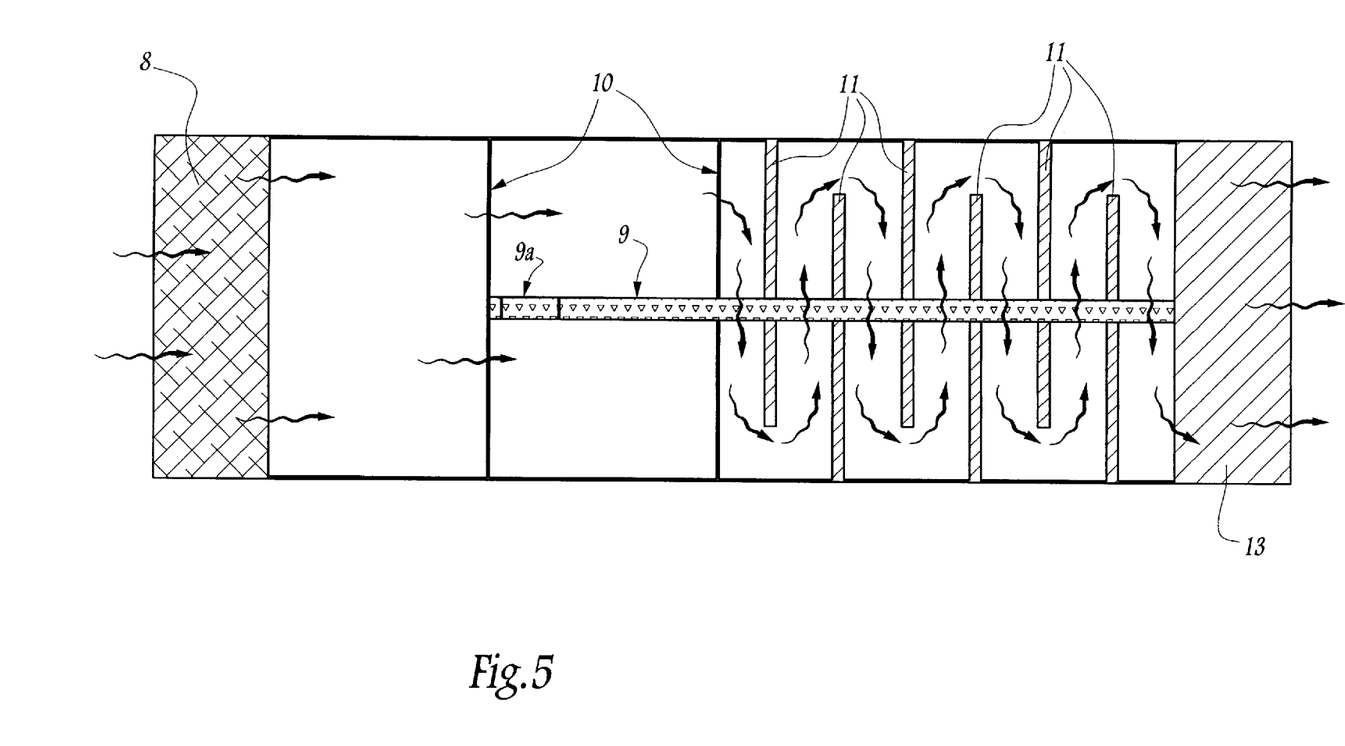
FIG. 5 illustrates a view along the sectional plane IV of the device according to claim 3.

FIG. 5 illustrates a device according to the invention comprising a mechanical filter (8), an adsorption supporting medium (13) and two juxtaposed chambers:

a first chamber comprising a biquartz lamp (9) emitting rays at 254 nm and rays at 185 nm emitted by the portion (9a), the internal walls (10) of this chamber being covered with a photocatalyst; and a second chamber comprising plates (11), the surface of which is covered with a photocatalyst and wherein extends the lamp (9) of the first chamber.

The air flows are materialized by the different arrow. The air flow comes into contact with or near the plates (11).

The present invention will now be described by means of a non-limiting example.

EXAMPLE

The method according to the invention was applied for treating polluted air comprising 900 ppm of ethylene and contained in a room of 54 m³.

The treatment device consists in two concentric cylindrical chambers and a mechanical pre-filter of the G3 type. The internal chamber comprises a biquartz lamp emitting radiations at 254 nm and at 185 nm (1 to 2% of the rays emitted being rays at 185 nm), the internal wall and the external wall of the internal chamber being covered with $TiO_2$. The external chamber comprises three lamps emitting rays at 254 nm, the internal wall of this chamber being covered with $TiO_2$.

The air passes into the treatment device at a rate of 400 m³/hour.

After 24 hours, the amount of ethylene in the air is 135 ppm.

This example shows that the method of the invention gives the possibility of obtaining depolluted air and this within a relatively short time.

The invention claimed is:

1. A method for purifying air comprising pollutants, comprising degrading all or part of the pollutants by the action of UV rays generated by a single two-quartz light source having two quartz parts including an upstream part emitting rays at 254 nm and ozone-producing rays at 185 nm, and a downstream part emitting rays at 254 nm, and by photocatalysis, the ratio between the amount of energy of the rays at 185 nm and the amount of energy of the rays at 254 nm ranging from 0.005 to 1, wherein the air is forced to circulate first in front of the upstream part, and then in front of the downstream part, the method comprising use of an adsorption supporting medium which comprises plates positioned against the passage of the air around at least the downstream part emitting rays at 254 nm so as to provide a forced passage for the air, which medium is covered by the photocatalyst, wherein upon passage of the air in contact with the photocatalyst, the pollutants and ozone are scavenged and subject to photocatalysis.

2. The method according to claim 1, wherein the ratio between the amount of energy of the rays at 185 nm and the amount of energy of the rays at 254 nm ranges from 0.01 to 0.2.

3. The method according to claim 1, wherein the ratio between the amount of energy of the rays at 185 nm and the amount of energy of the rays at 254 nm ranges from 0.005 to 0.05.

4. The method according to claim 1, wherein the photocatalysis is applied in the presence of a supported photocatalyst comprising titanium or tungsten.

5. The method according to claim 4, wherein the photocatalyst is supported TiO2.

6. The method according to claim 1, comprising a preliminary step of mechanical filtering of air.

7. A device adapted for applying the method according to claim 1, comprising a chamber comprising:

a single two-quartz light source having two quartz parts including a first upstream part emitting rays at 254 nm and ozone-producing rays at 185 nm, and a second downstream part emitting rays at 254 nm, and a photocatalyst, the ratio between the amount of energy of the rays at 185 nm and the amount of energy of the rays at 254 nm ranging from 0.005 to 1; and an adsorption supporting medium which comprises plates positioned against the passage of the air around at least the second part emitting rays at 254 nm so as to provide a forced passage for the air, said medium being covered by the photocatalyst, wherein upon passage of the air in contact with the photocatalyst, the pollutants and ozone are scavenged and subjected to photocatalysis.

8. The device according to claim 7, wherein the ratio between the amount of energy of the rays at 185 nm and the amount of energy of the rays at 254 nm ranges from 0.01 to 0.2.

9. The device according to claim 7, wherein the ratio between the amount of energy of the rays at 185 nm and the amount of energy of the rays at 254 nm ranges from 0.005 to 0.05.

10. The device according to claim 7 wherein the adsorption supporting medium is selected from the group consisting of silica, quartz, glass fabric, quartz fabric, silica fabric, glass fibers, optical fiber fabric, and ceramic.

11. The device according to claim 7, comprising two concentric chambers:

an internal chamber (1) comprising a single light source emitting rays at 254 nm and 185 nm and a photocatalyst, the ratio between the amount of energy of the rays at 185 nm and the amount of energy of the rays at 254 nm ranging from 0.005 to 1; and an external chamber (2) comprising at least one second light source emitting rays at 234 nm, a photocatalyst and optionally an adsorption supporting medium, the walls of the chambers (1) and (2) being permeable to air.

12. The device according to claim 7 comprising two juxtaposed chambers:

a chamber (1) comprising a single light source emitting rays at 254 nm and 185 nm and a photocatalyst, the ratio between the amount of energy of the rays at 185 nm and the amount of energy of the rays at 254 nm ranging from 0.005 to 1;

a chamber (2) comprising all or part of the quartz of the single source only emitting rays at 254 nm, a photocatalyst and optionally an adsorption supporting medium, only the walls separating the different chambers from each other being permeable to air.

13. The device according to claim 7, further comprising a mechanical air filter.

* * * * *